United States Patent [19]
Alfano et al.

[11] Patent Number: 6,091,985
[45] Date of Patent: Jul. 18, 2000

[54] DETECTION OF CANCER AND PRECANCEROUS CONDITIONS IN TISSUES AND/OR CELLS USING NATIVE FLUORESCENCE EXCITATION SPECTROSCOPY

[75] Inventors: Robert R. Alfano, Bronx, N.Y.; Singaravelu Ganesan, Edison, N.J.; Alvin Katz, Bronx; Yang Yuanlong, New York, both of N.Y.

[73] Assignee: Research Foundation of City College of New York, New York, N.Y.

[21] Appl. No.: 09/012,482

[22] Filed: Jan. 23, 1998

Related U.S. Application Data

[60] Provisional application No. 60/035,650, Jan. 23, 1997.

[51] Int. Cl.[7] ....................................................... A61B 5/00
[52] U.S. Cl. ............................ 600/476; 600/477; 436/63; 436/64; 436/172
[58] Field of Search ................................... 600/476–478, 600/473, 475; 436/63, 64, 172

[56] References Cited

U.S. PATENT DOCUMENTS

| | | | |
|---|---|---|---|
| 4,270,924 | 6/1981 | Crooke et al. | 436/64 |
| 5,131,398 | 7/1992 | Alfano et al. | 600/477 |
| 5,456,260 | 10/1995 | Kollias et al. | 600/477 |
| 5,635,402 | 6/1997 | Alfano et al. | 436/63 |
| 5,697,373 | 12/1997 | Richards-Kortum et al. | 600/473 |

*Primary Examiner*—Ruth S. Smith
*Attorney, Agent, or Firm*—Kriegsman & Kriegsman

[57] ABSTRACT

A method of detecting cancer or precancerous conditions in a tissue or cell using fluorescence excitation spectroscopy. According to one embodiment of the method, a tissue is tested for cancer or a precancerous condition by exciting the tissue with substantially monochromatic light at 268 nm and then at 289 nm, with the resultant native fluorescence emitted from the tissue following each excitation being measured. A ratio of the fluorescence intensities, e.g., $I_{289}/I_{268}$, is then calculated. If $I_{289}/I_{268}$ is greater than 1.5, the tissue is cancerous or precancerous whereas if $I_{289}/I_{268}$ is less than 1.5, the tissue is not cancerous or precancerous.

43 Claims, 11 Drawing Sheets

DETECTION OF CANCER AND PRECANCEROUS CONDITIONS IN TISSUES AND/OR CELLS USING NATIVE FLUORESCENCE EXCITATION SPECTROSCOPY

CROSS-REFERENCE TO RELATED APPLICATIONS

The present application claims the benefit under 35 U.S.C. 119(e) of U.S. Provisional Patent Application Ser. No. 60/035,650, filed Jan. 23, 1997, the disclosure of which is incorporated herein by reference.

BACKGROUND OF THE INVENTION

The present invention relates generally to the detection of cancer and precancerous conditions and more particularly to a method of detecting the presence of cancer and/or precancerous conditions in tissues and/or cells using native fluorescence excitation spectroscopy. The present invention also relates to the detection of the presence of cancer-related proteins in tissues and/or cells using native fluorescence excitation spectroscopy.

Because a sufficiently effective method has not yet been developed to prevent cancer, cancer research has focused on the most effective ways to treat cancer. As different as the various forms of treatment have been—ranging from excision to radiation to chemotherapy—all treatments have relied upon one crucial step, the detection of cancer. The importance of detection cannot be stressed enough. Early detection not only indicates the presence of cancer (or of a precancerous condition) but also may give an indication as to where the cancer originated and what type of treatment will be the most safe and effective. In addition to being used to detect cancer early, detection methods may also be used to determine whether treatment methods have been successful in eradicating cancer from a patient.

At present, methods for detecting most forms of cancer have relied primarily on the use of X-rays, nuclear magnetic resonance, nuclear radiation or invasive methods based on chemical laboratory analysis and biopsy. More recently, optical spectroscopy has been investigated as a means of detecting cancer.

For example, in U.S. Pat. No. 4,930,516, inventors Alfano et al., which issued Jun. 5, 1990, and which is incorporated herein by reference, there is disclosed a method and apparatus for detecting the presence of cancerous tissue using visible luminescence. According to the aforementioned patent, the tissue to be examined is excited with a beam of monochromatic light that causes the tissue to fluoresce over a spectrum of wavelengths. The monochromatic light disclosed in the patent has a wavelength in the range of 350–500 nm. The intensity at which the excited tissue fluoresces is measured either over a spectrum or at a predetermined number of preselected wavelengths, such as at 531 nm, 522 nm and 633 nm. The patent further teaches that one can then determine the carcinomatoid status of the tissue in question by comparing the detected spectrum, one or more peak wavelengths of the detected spectrum, or a ratio or difference of particular wavelengths from the detected spectrum to standards obtained from known tissues.

In U.S. Pat. No. 5,042,494, inventor Alfano, which issued Aug. 27, 1991, and which is incorporated herein by reference, there is disclosed a method and apparatus for detecting the presence of cancerous tissue using native visible luminescence. In accordance with said patent, the tissue to be examined is excited with a beam of monochromatic light having a changeable wavelength that causes the tissue to fluoresce. The intensity at which the excited tissue fluoresces at a preselected wavelength is then measured. The patent discloses that an excitation spectrum for human breast tissue was obtained by scanning from 300 nm to 500 nm at an emission wavelength of 520 nm. The patent further teaches that one can then determine the carcinomatoid status of the tissue in question by comparing the detected excitation spectrum, one or more peak wavelengths of the detected excitation spectrum, or a ratio or difference of particular wavelengths from the detected excitation spectrum to standards obtained from known tissues.

In U.S. Pat. No. 5,131,398, inventors Alfano et al., which issued Jul. 21, 1992, and which is incorporated herein by reference, there is disclosed a method and apparatus for distinguishing cancerous tumors and tissue from benign tumors and tissue or normal tissue using native fluorescence. According to one embodiment of said patent, the tissue to be examined is excited with a beam of monochromatic light at 300 nm. The intensity of the native fluorescence emitted from the tissue is measured at 340 nm and at 440 nm. The ratio of the two intensities is then calculated and used as a basis for determining if the tissue is cancerous as opposed to benign or normal. According to another embodiment of said patent, excitation profiles may be employed to distinguish cancerous tissue from benign or normal tissue. For example, the patent teaches that excitation spectra obtained by measuring the intensity of fluorescence at 340 nm as the excitation wavelength is varied from 220 nm to 325 nm are different for cancerous and benign breast tissues.

In U.S. Pat. No. 5,413,108, inventor Alfano, which issued May 9, 1995, and which is incorporated herein by reference, there is disclosed a method and apparatus for examining a two-dimensional region of a tissue sample. In accordance with said patent, this is accomplished by illuminating, i.e., exciting, the two-dimensional tissue sample with light at a first wavelength. The resultant fluorescence is then measured at an emission wavelength as a function of location within the two-dimensional tissue sample. The two-dimensional tissue sample is then illuminated again with light at a second wavelength, and the resultant fluorescence is measured at the same emission wavelength. The two excitation wavelengths and the emission wavelength are appropriately chosen so that the ratio or difference of fluorescence intensities at the emission wavelength is indicative of the carcinomatoid condition of the tissue. A value, such as a ratio or difference, of the respective intensity measurements obtained at each location of the tissue sample is then calculated. These values are then compared to appropriate standards, and the results are depicted in the form of a map. The invention is premised on the discovery that certain native, commonly-occurring molecules, such as collagen, NAD+/NADH, NADP+/NADPH, flavins, tryptophan and elastin, fluoresce differently in cancerous tissue than in non-cancerous tissue.

SUMMARY OF THE INVENTION

It is an object of the present invention to provide a novel technique for detecting cancer and precancerous conditions in tissues and/or cells.

It is another object of the present invention to provide a novel technique as described above that employs native fluorescence excitation spectroscopy.

The present invention is based, in part, on the discovery that the native fluorescence excitation spectra, measured at 340 emission with excitation over the 250 nm to 320 nm spectral region, for malignant tissues and cells are distinguishable from the corresponding excitation spectra for normal tissues and cells.

Consequently, according to one aspect of the invention, there is described a method of detecting cancer or a precancerous condition in a tissue and/or cell comprising the steps of (a) obtaining a fluorescence excitation spectrum of the tissue or cell with emission in the range of about 330 nm to about 400 nm and excitation over a spectral region of about 250 nm to about 320 nm or with emission in the range of about 350 nm to about 450 nm and excitation over a spectral region of about 260 nm to about 340 nm; and (b) comparing said fluorescence excitation spectrum to standard spectra obtained from known normal and cancerous or precancerous samples.

It is another object of the present invention to provide a novel technique for detecting the presence of cancer-related, mutant proteins in samples, such as tissue samples and/or cell samples.

This aspect of the present invention is based, in part, on the discovery that certain mutant forms of naturally-occurring proteins are related to the development of certain types of cancer and precancerous conditions.

Consequently, according to another aspect of the invention, there is described a method of detecting the presence of a cancer-related, mutant protein in a tissue and/or cell comprising the steps of (a) illuminating the sample with substantially monochromatic light of a first excitation wavelength so as to cause the sample to emit native fluorescence at an emission wavelength, said first excitation wavelength being in the range of about 250 nm to about 320 nm, said emission wavelength being in the range of about 330 nm to about 400 nm; (b) measuring the intensity of native fluorescence at said emission wavelength caused by excitation of said sample at said first excitation wavelength; (c) illuminating the sample with substantially monochromatic light of a second excitation wavelength so as to cause the sample to emit native fluorescence at said emission wavelength, said second excitation wavelength being in the range of about 250 nm to about 320 nm; (d) measuring the intensity of native fluorescence at said emission wavelength caused by excitation of said sample at said second excitation wavelength; (e) calculating a ratio of intensities measured at said emission wavelength corresponding to excitation at said first and second excitation wavelengths; and (f) determining whether or not the sample contains the cancer-related protein based on said ratio.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

As noted above, the present invention is based, in part, on the discovery that certain mutant forms of naturally-occurring proteins are related to the development of certain types of cancer and precancerous conditions in a patient. For example, researchers have recently discovered that mutant forms of the P53, BRCA-1 and BRCA-2 proteins are related to the development of breast cancer in women. See e.g., Chen et al., Science, 270:789–91 (1995); Miki et al., Science, 266, 66–71 (1994); Easton et al., Am. J. Hum. Genet., 52:678–701 (1993); and Begley, "The Cancer Killer," Newsweek, 42–47 (Dec. 13, 1996), all of which are incorporated herein by reference. The role of the BRCA protein appears to be to attach itself to genetic material in the cell nucleus and to control the switching on and off of certain genes. Researchers have found that, in the rare familial form of breast cancer, a mutant form of the BRCA-1 protein is made which is inoperable. Due to the presence of this inoperable mutant form of BRCA-1, cell division is unregulated and cancer develops. In the more common forms of breast cancer, a mutant form of the BRCA-1 protein is produced that is incapable of entering the cell nucleus.

In addition, mutant forms of other proteins are believed to be involved in the development of cancers of the colon, lung, bladder, skin, prostate and cervix.

The present invention is also based, in part, on the discovery that the fluorescence excitation spectra, measured at about 340 nm with excitation over the 250 nm to 320 nm spectral region, for malignant tissues and cells (in which the aforementioned cancer-related, mutant proteins are presumably present) are distinguishable from corresponding spectra for benign or normal tissues and cells (in which said proteins are presumably not present).

Accordingly, using the aforementioned discoveries, one feature of the present invention is a method of detecting the presence of said mutant proteins in a tissue and/or cell using fluorescence excitation spectroscopy. One advantage associated with the method of the present invention is that it is possible for those tissues and cells harboring the mutant proteins to be identified prior to their development of physical signs of cancer or of precancerous conditions. In this manner, cancers can be identified at their earliest stages, perhaps even before precancers form. In addition, suspect tissue regions which exhibit the salient spectral features indicative of the mutant proteins can be monitored, removed or modified. Moreover, because these types of proteins may be present in areas other than those where cancers actually develop, the presence of these proteins in one location of a body can serve as an indicator that larger areas of the body need to be examined in detail.

As a technical underpinning for the present invention, the present inventors conducted certain studies on the native fluorescence of malignant and benign human breast tissues. (See Yang et al., "Fundamental Differences of Excitation Spectrum between Malignant and Benign Breast Tissues," *Photochemistry and Photobiology*, 66(4):518–22 (1997) and Yang et al., "Excitation Spectrum of Malignant and Benign Breast Tissues: A Potential Optical Biopsy Approach," *Lasers in the Life Sciences*, 7(4):249–65 (1997), both of which are incorporated herein by reference.)

Spectroscopic measurements were performed using an automated lamp-based spectrometer, CD Scan from Mediscience Technology Corp. (Cherry Hill, N.J.). Seven excitation scans (275 nm excitation/295–520 nm emission; 300 nm excitation/320–580 nm emission; 325 nm excitation/345–620 nm emission; 340 nm excitation/360–650 nm emission; 360 nm excitation/380–650 nm emission; 400 nm excitation/450–650 nm emission and 450 nm excitation/470–650 nm emission), five emission scans (340 nm emission/250–320 nm excitation; 360 nm emission/250–340 nm excitation; 380 nm emission/250–360 nm excitation; 450 nm emission/250–430 nm excitation; and 630 emission/350–550 nm excitation) and one diffusive reflectance scan (from 300 nm to 650 nm) were measured on 63 benign (also referred to herein as "normal") human breast specimens and 103 malignant human breast specimens. The breast tissue samples were obtained from dissected specimens from St. Vincent Medical Center of Staten Island by Dr. E. Celmer. Specimens were not chemically treated prior to taking the measurements. Samples of random shape were mounted in quartz cuvettes for spectroscopic studies. At least three sites on each specimen were measured. The process of spectroscopic measurement was a blind study. After measurement, the samples were returned for pathological determination. Pathology was used as the standard against which the spectroscopic diagnoses were compared. The pathological classification of the specimens is given in Table I below. As can be seen, most of the malignant tissues were ductal carcinoma and most of the benign tissues were benign breast tissue and fibercystic change. The benign tumor was fibroadenoma.

TABLE I

| SAMPLE | DESCRIPTION | TOTAL |
| --- | --- | --- |
| BENIGN NO. 1 | Benign breast tissue | 15 |
| BENIGN NO. 2 | Fibrocystic change | 44 |
| BENIGN NO. 3 | Benign lymph node | 1 |
| BENIGN NO. 4 | Lactating breast | 3 |
| MALIGNANT NO. 1 | Ductal carcinoma | 80 |
| MALIGNANT NO. 2 | Lobular carcinoma | 6 |
| MALIGNANT NO. 3 | Metastatic breast carcinoma | 7 |
| MALIGNANT NO. 4 | Mucinous carcinoma | 3 |
| MALIGNANT NO. 5 | Poorly differentiated carcinoma | 5 |
| MALIGNANT NO. 6 | Pleomorphic sarcoma | 2 |

Figure 1:
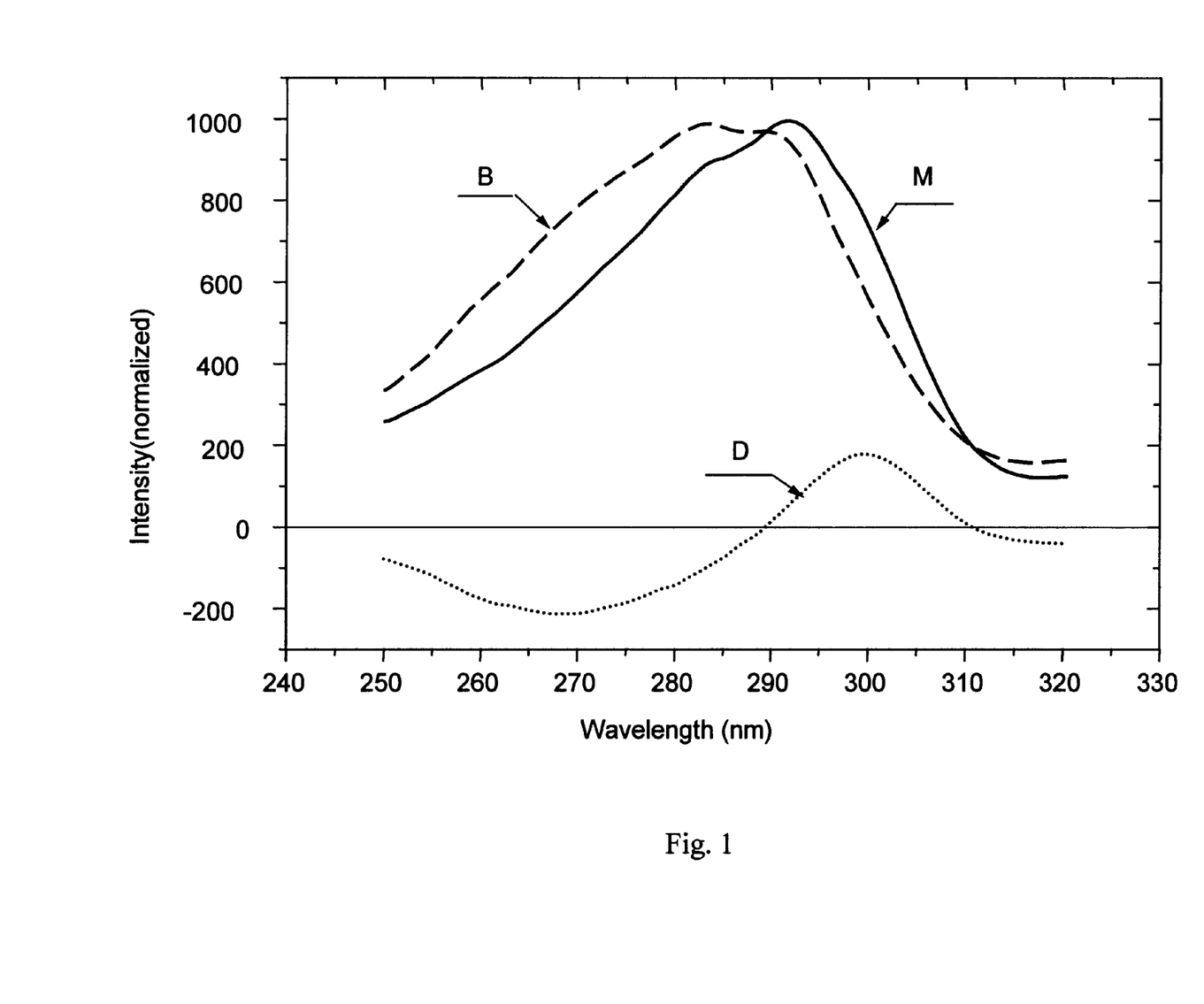
FIG. 1 is a graphic representation of the averaged excitation spectra measured at 340 nm emission with excitation over the 250 nm to 320 nm spectral region for twenty-three benign (B) and thirty-two malignant (M) human breast tissue samples, respectively (a difference spectrum (D) representing M-B also being depicted)
Figure 2:
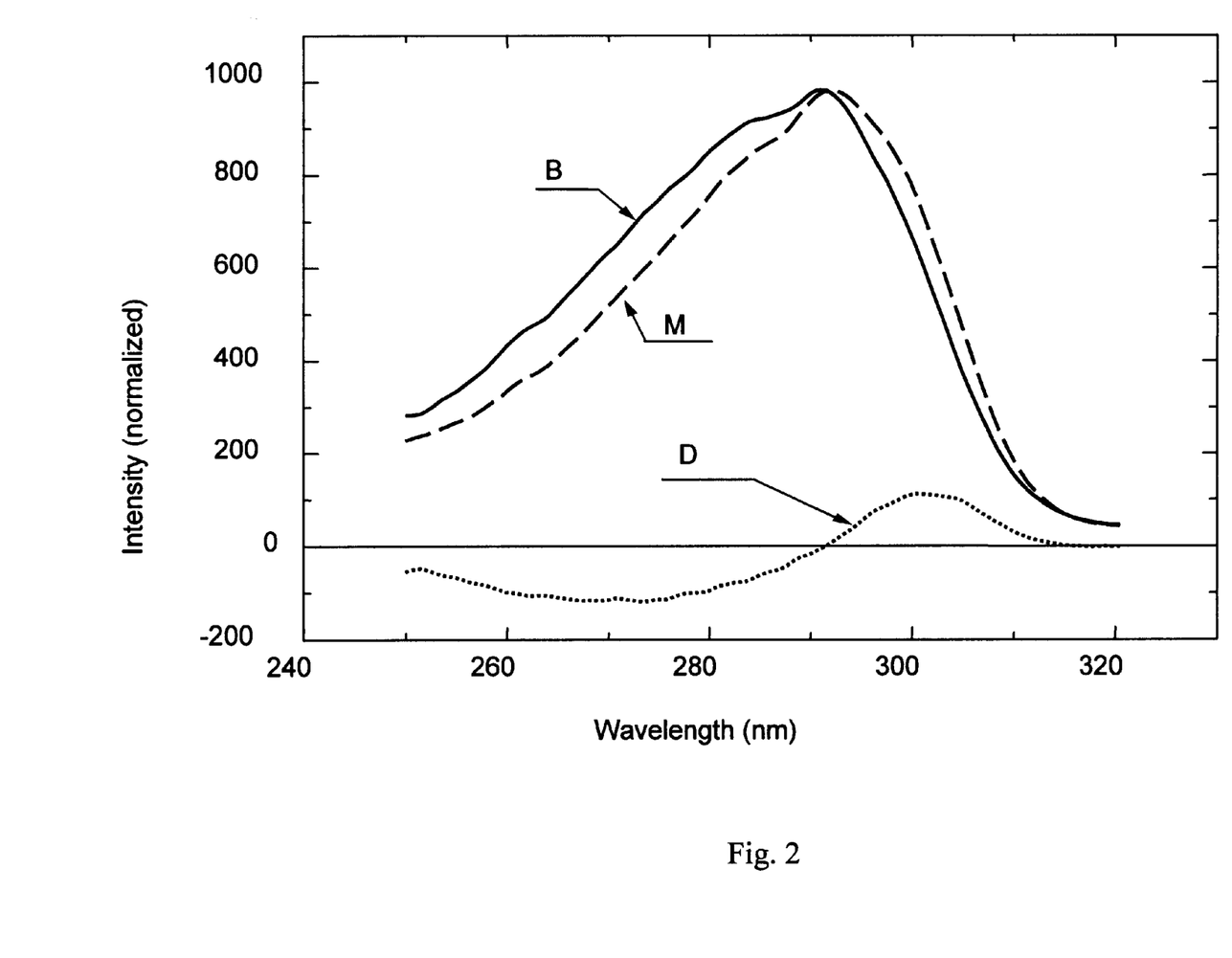
FIG. 2 is a graphic representation of the averaged excitation spectra measured at 340 nm emission with excitation over the 250 nm to 320 nm spectral region for thirty-six benign (B) and thirty-four malignant (M) human colon tissue samples, respectively (a difference spectrum (D) representing M-B also being depicted)

The averaged excitation spectra for emission at 340 nm for the above-described 63 benign and 103 malignant breast tissue samples are shown in FIG. 1. The averaged curves for benign and malignant colon tissues are shown in FIG. 2. These spectra were obtained by normalizing the peak of each curve to unity prior to averaging. The averaged spectra (and their standard deviations) clearly show spectral differences between malignant and benign tissue, especially in breast tissue.

The salient features of the averaged spectra of the breast tissues shown in FIG. 1 are as follows: (1) Two intensity peaks near 283 nm and 292 nm, respectively, are observed for benign tissues. The peak near 292 nm still exists but is shifted to the right of the benign peak and the 283 nm peak is decreased for malignant tissues. (2) A normalized isosbestic point was observed at 289±3 nm for the tissue samples. At this point, the averaged excitation spectra of malignant and benign tissues showed no change. (3) The intensity, relative to 289 nm, for benign tissue in the 250–289 nm spectral range is higher than that of the malignant tissue, which results in a negative value in the difference spectrum. The situation is reversed for the 289–310 nm range, causing the difference spectrum to be positive.

Two diagnostic parameters were introduced to quantify these observations, $R_1=I_{289}/I_{268}$ and $R_2=I_{289}/I_{300}$, where $I_{268}$ and $I_{300}$ are the relative intensities at peak positions for the difference spectrum, and $I_{289}$ is the relative intensity at the normalized isosbestic point. The averaged ratio value of $R_1$ is 1.79±0.22 for malignant tissue and 1.30±0.13 for benign tissue. The relative absorption at 268 nm compared to 289 nm for malignant tissue is lower by 27% than that for benign tissue. The averaged ratio value of $R_2$ is 1.39±0.21 for malignant and 1.74±0.22 for benign tissue. The relative absorption at 300 nm compared to the isosbestic point (289 nm) for malignant tissue is 25% higher than benign tissue. In other words, when breast tissue changes from normal to malignant, the relative absorption is decreased at 268 nm, but increased at 300 nm. These ratio parameters are displayed in Table II.

TABLE II

| TISSUE TYPE | $R_1 = I_{289}/I_{268}$ | $R_2 = I_{289}/I_{300}$ |
|---|---|---|
| Malignant | 1.79 ± 0.22 | 1.39 ± 0.21 |
| Normal | 1.30 ± 0.13 | 1.74 ± 0.22 |

Figure 3:
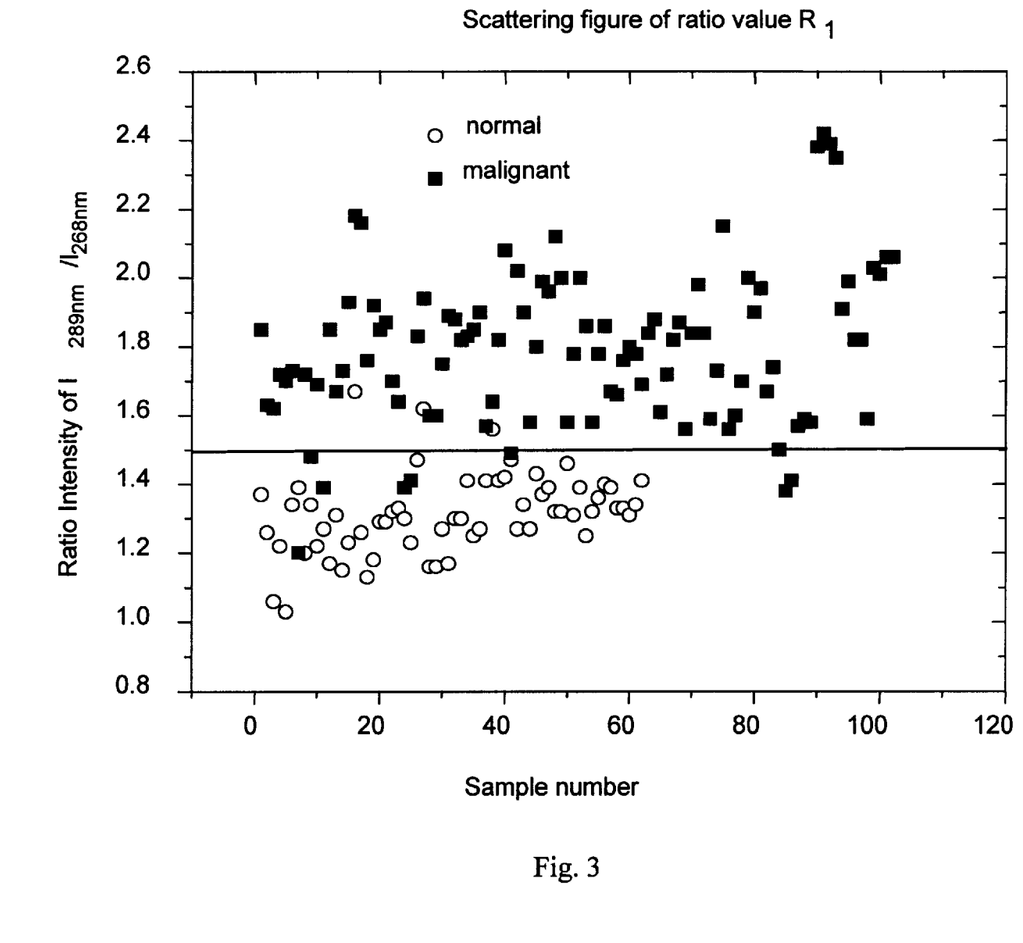
FIG. 3 is a graphic representation of the ratio of the fluorescence intensity at 289 nm excitation (340 nm emission) to the fluorescence intensity at 268 nm excitation (340 nm emission) for a number of benign and malignant human breast tissue samples.
Figure 4:
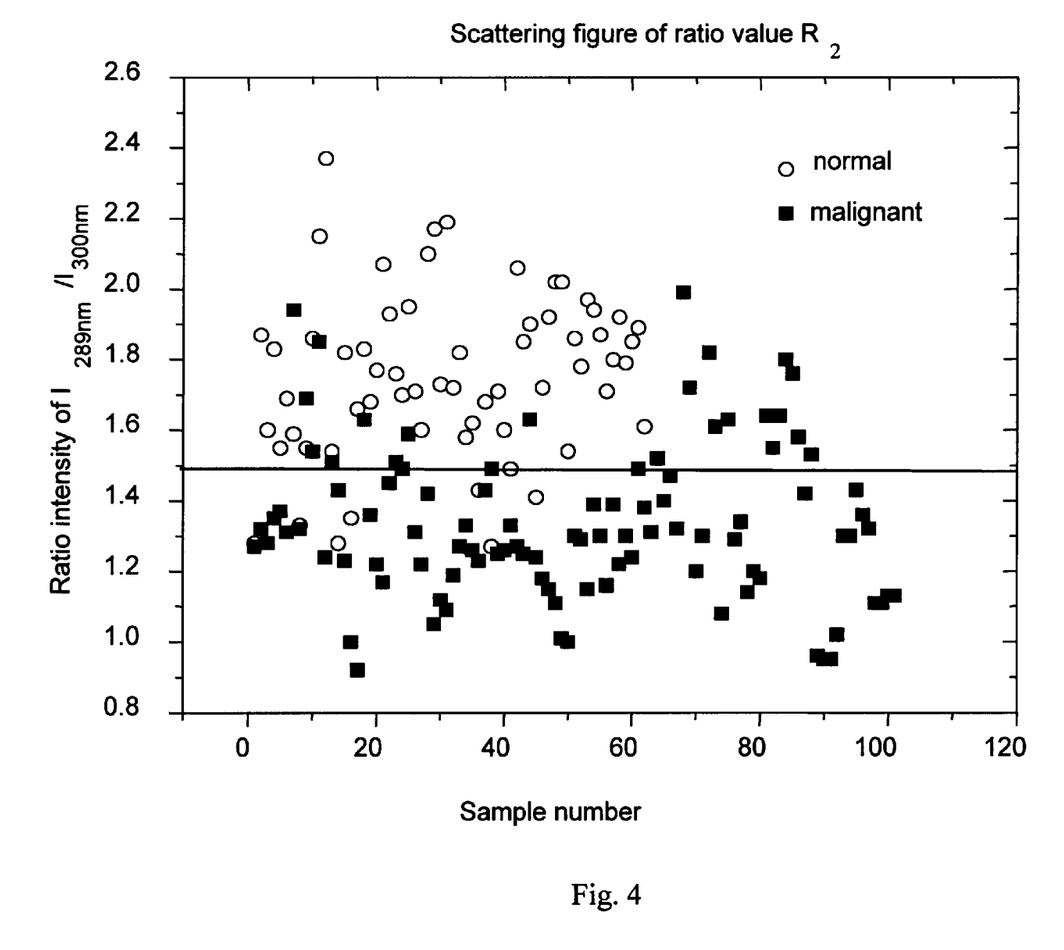
FIG. 4 is a graphic representation of the ratio of the fluorescence intensity at 289 nm excitation (340 nm emission) to the fluorescence intensity at 300 nm excitation (340 nm emission) for a number of benign and malignant human breast tissue samples.

The scatter plots of the ratio values $R_1$ and $R_2$ for the malignant and normal human breast tissue samples are shown in FIGS. 3 and 4. From these figures, it can be seen that a value of 1.5 can be used as a criterion to separate malignant from benign breast tissues. The statistical results using these two critical parameters (R1 and R2) to separate malignant from benign breast tissues are displayed in TABLES IIIA and IIIB.

TABLE IIIA

| NORMAL | $R_1 = I_{289}/I_{268}$ | | $R_2 = I_{289}/I_{300}$ | |
|---|---|---|---|---|
| | Correct | False | Correct | False |
| Benign breast tissue (15) | 14 | 1 | 13 | 2 |
| | 93% | 7% | 87% | 13% |
| Fibrocystic change (44) | 43 | 1 | 41 | 3 |
| | 98% | 2% | 93% | 7% |
| Benign lymph node (1) | 1 | 0 | 0 | 1 |
| Lactating breast (3) | 2 | 1 | 2 | 1 |
| Total (63) | 60 | 3 | 56 | 7 |
| | 95% | 5% | 89% | 11% |

TABLE IIIB

| MALIGNANT | $R_1 = I_{289}/I_{268}$ | | $R_2 = I_{289}/I_{300}$ | |
|---|---|---|---|---|
| | Correct | False | Correct | False |
| Ductal carcinoma (80) | 78 | 2 | 68 | 12 |
| | 97% | 3% | 85% | 15% |
| Lobular carcinoma (6) | 1 | 5 | 0 | 6 |
| Metastatic breast carcinoma (7) | 7 | 0 | 7 | 0 |
| Pleomorphic sarcoma (2) | 2 | 0 | 2 | 0 |
| Mucinous carcinoma (3) | 3 | 0 | 1 | 2 |
| Poorly differentiated carcinoma (5) | 5 | 0 | 5 | 0 |
| Total (103) | 96 | 7 | 83 | 20 |
| | 93% | 7% | 80% | 20% |

The specificity and sensitivity for parameters $R_1$ and $R_2$ were obtained using pathological examination as the standard. A student t-test to determine the difference between malignant and benign tissues for the ratios $R_1$ and $R_2$ has been calculated. The P value for these ratios is less than 0.001.

The changes in the excitation spectrum of colon tissue shown in FIG. 2 are similar to those of breast tissue but less pronounced. These similarities indicate that colon neoplasm may exhibit the presence of mutant protein changes associated with cancer.

Figure 5:
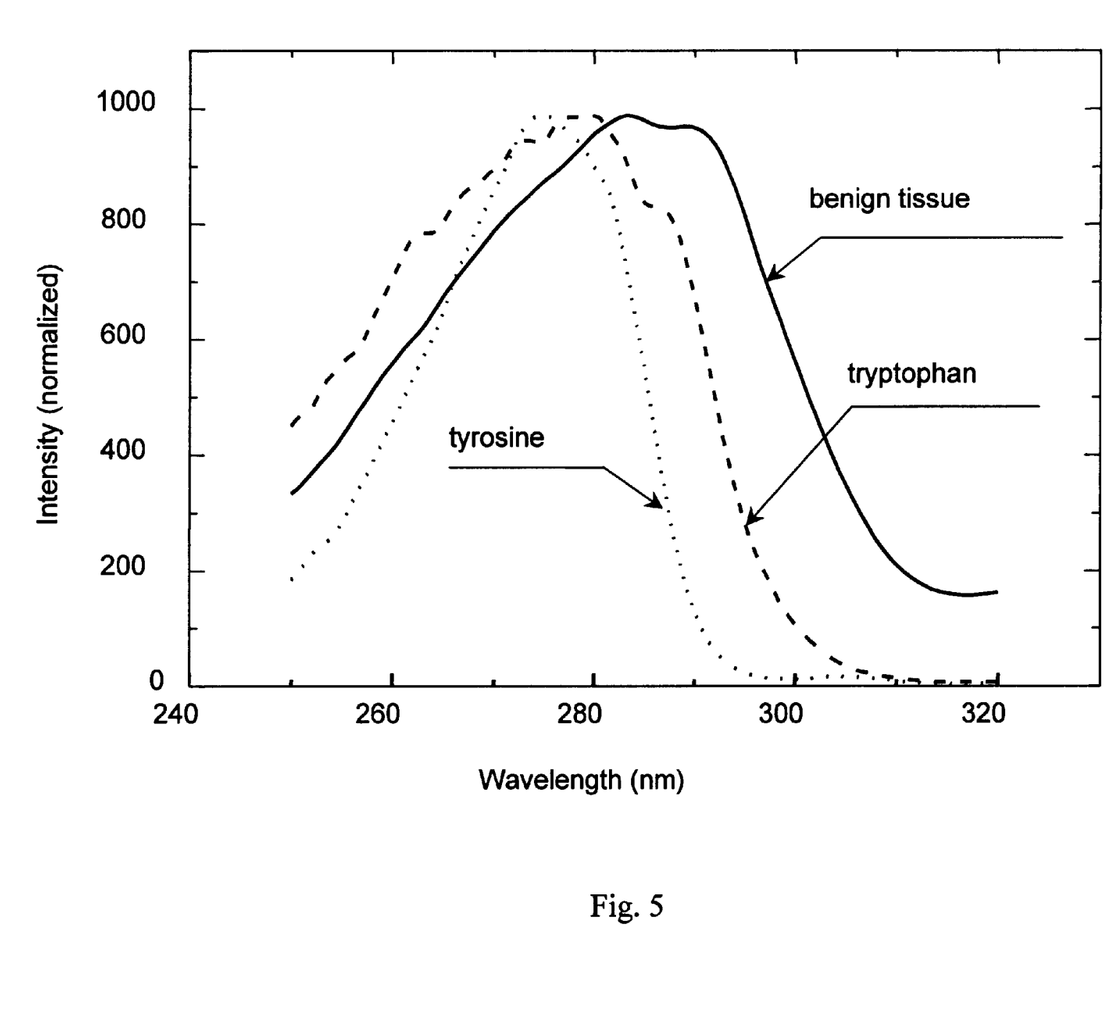
FIG. 5 is a graphic representation of the excitation spectra measured at 340 nm emission with excitation over the 250 nm to 320 nm spectral region for benign human breast tissue, tyrosine in water and tryptophan in water, respectively.

Although not wishing to be limited to any particular theory as to why the observed excitation spectra for malignant and normal tissues are distinguishable, the present inventors believe that the differences in the respective spectra are due to changes associated with key amino acids in the tissue proteins, such as phenylalanine, tyrosine and tryptophan. To check this theory, the excitation spectra of certain amino acids in water were measured. For example, as seen in FIG. 5, the excitation spectra of tryptophan in water and tyrosine in water were obtained and compared to that of benign tissue. In addition, key optical parameters of certain amino acid solutions are listed in TABLE IV.

TABLE IV

| Amino Acid in water at 293° K. | Extinction Coefficient $m^2mol^{-1}$ | Absorption Peak (nm) | Fluorescence Peak (nm) | Fluorescence Quantum Yield |
|---|---|---|---|---|
| phenylalanine | 19.7 | 253 | 282 | 0.04 |
| tyrosine | 142–185 | 275 | 303 | 0.20 |
| tryptophan | 560–617 | 280 | 348 | 0.20 |

As can be seen in FIG. 5, the spectra of the amino acid solutions show similar profiles to that of tissue, but with a 10 nm blue shift. This blue shift is most likely due to the differences in the tissue environment. The excitation spectrum change is related to the change in optical absorption by molecules that cause the 340 nm emission. Experimental results show that the change in the excitation spectrum from 250 nm to 320 nm should be related to the change in the amount of amino acids and, consequently, to the proteins and changes in the local environment. Changes observed in excitation spectra in the spectral region of 250 nm to 289 nm indicate either a relative decrease of certain amino acids or modifications to the conformation of the protein experienced when the tissue changes from benign to malignant. The differences in the excitation spectra may be associated with the different location in a cell of a protein like BRCA-1 since these differences in the excitation spectra can be associated with the criteria to diagnose malignant tissue from benign tissue with over 90% consistency.

Furthermore, spectral differences in the 290–310 nm range show an increase for malignant tissue as compared to benign tissue. This increase may be attributable to an increase in the concentration of certain amino acids in a new form of the protein or in an environmental change experienced by cell proteins. There are 10 tryptophan residues, 25 tyrosine residues and 34 phenylalanine residues in one BRCA-1 molecule. The change in the observed excitation spectra may be related to these amino acids since difference uv excitation spectroscopy nulls out, in part, common protein contributions, thereby leaving those proteins associated with a change.

The experiments described above relate to the testing of tissues. To assess the applicability of the principles described above to cells, the present inventors conducted certain studies on the native fluorescence of human epithelial cells. Two types of epithelial cells were used. The malignant squamous carcinoma cell line, 1483, was maintained in log phase culture in DMEM-F12 medium supplemented with 10% fetal calf serum and gentamicin (50 μg/ml), as described in Sacks et al., *Cancer Res.*, 48:2858–66 (1988), which is incorporated herein by reference. Normal (also referred to herein as "benign") human epithelial cells were derived from anterior tonsillar pillar mucosa obtained from routine tonsillectomies. Primary cultures were established in AmnioMax C-100 (Gibco, Grand Island, N.Y.) using explant outgrowth technique and first passaged cells were maintained in KGM (Clonetics, San Diego, Calif.), as described in Xu et al., *Methods in Cell Science*, 18:1–9 (1996), which is incorporated herein by reference. Log phase cells were trypsinized and washed 3× in phosphate buffered saline. Cell viability as measured by trypan blue exclusion was always over 90%. Cells, at a concentration of $5 \times 10^6$ per ml, were packed in a 5 mm path length quartz cuvette and fluoresced at room temperature (23° C.) within three hours of harvesting.

Native steady state fluorescence spectra from both normal and malignant oral cells were measured with CD-Scan (Mediscience Technology Corp., Cherry Hill, N.J.). The cell samples were placed in a quartz cuvette of 5 mm path length, and the native cellular fluorescence excitation spectra were measured at excitation wavelengths in the range of 250–320 nm for 340 nm emission. The fluorescence emission spectra were analyzed for excitation at 275, 285 and 310 nm.

Figure 6:
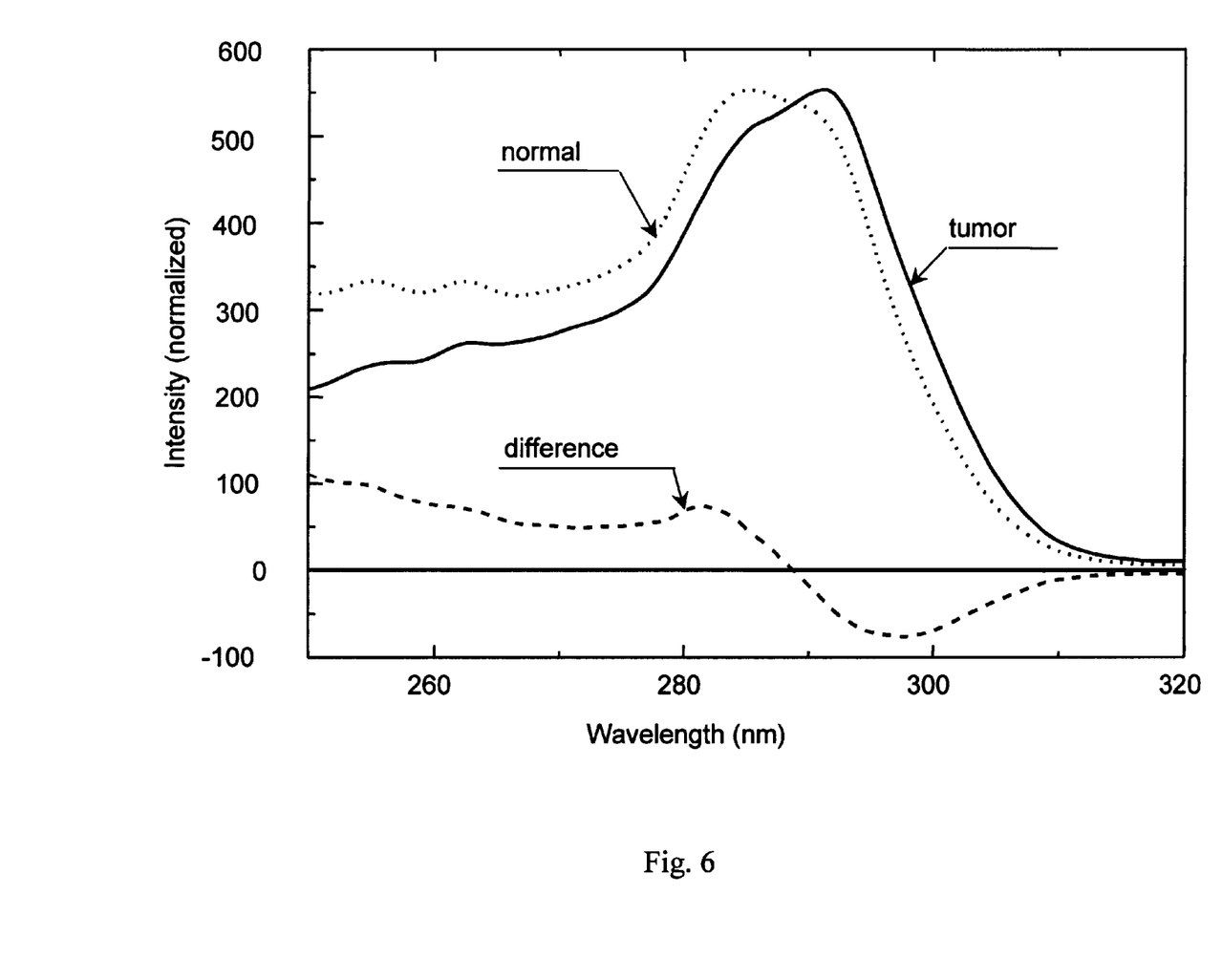
FIG. 6 is a graphic representation of the averaged excitation spectra measured at 340 nm emission with excitation over the 250 nm to 320 nm spectral region for a number of normal human epithelial cells derived from anterior tonsillar pillar mucosa and for a number of malignant human squamous cells, respectively (a difference spectrum (D) representing M-B also being depicted)

The averaged excitation spectra with 340 nm emission for the foregoing normal and malignant human epithelial cells excited over the 250 nm to 320 nm spectral region is shown in FIG. 6. The average spectra were obtained by normalizing the peak of each curve to unity and averaging. From these spectra, it is apparent that there is a spectral difference between malignant and benign cells. More particularly, the following salient features between the normal and malignant curves are noted: (1) Two intensity peaks near 283 nm and 292 nm are observed for normal and malignant epithelial cells, respectively. The peak near 292 nm increases for malignant cells, and the peak around 283 nm decreases for malignant cells. (2) A normalized isosbestic point is observed at 289±2 nm for the cells. At this isosbestic point, the averaged excitation spectra of malignant and normal cells do not differ. (3) The intensity for normal cells in the 250–289 nm spectral region is higher than that for the malignant cells; consequently, the difference spectra is negative over this region. By contrast, the intensity for malignant cells in the 289–297 nm spectral region is higher than that for the normal cells; consequently, the difference spectrum is positive over this region. (4) The spectrum for the malignant cells is red-shifted as compared to that for the normal cells.

In an effort to quantify the above-discussed differences, the present inventors introduced two ratio parameters: $R_{e1} \equiv I_{289}/I_{250}$ and $R_{e2} \equiv I_{289}/I_{297}$ wherein $I_{297}$ and $I_{250}$ are the relative intensities of peak positions of the difference spectrum, and $I_{289}$ is the relative intensity at the "normalized isosbestic" point. The averaged ratio value of $R_{e1}$ is 2.86±0.52 for the malignant cells and 1.66±0.06 for the normal cells. This is due to the fact that the relative absorption at 250 nm, as compared to 289 nm, is lower for malignant cells than for normal cells. Similarly, the value of $R_{e2}$ is 1.36±0.14 for malignant cells and 1.86±0.05 for normal cells. This is because the relative absorption around 297 nm, as compared to 289 nm, is higher for malignant cells than for normal cells. Using the student t-test, statistical significance was observed for $R_{e1}$ and $R_{e2}$ values between normal and malignant cells. The p value for both ratios was found to be p~0.0001, indicating a very high significance result for separating cell type. These results were obtained by averaging six individual curves for malignant (squamous cell carcinoma) and the normal cells of head and neck. These results are summarized in TABLE V.

TABLE V

| RATIO VALUE | NORMAL CELLS | MALIGNANT CELLS | p VALUE |
| --- | --- | --- | --- |
| $R_{e1} = I_{289}/I_{250}$ | 1.66 ± 0.06 | 2.86 ± 0.52 | 0.0001 |
| $R_{e2} = I_{289}/I_{297}$ | 1.86 ± 0.05 | 1.36 ± 0.14 | 0.0001 |

Figure 7A:
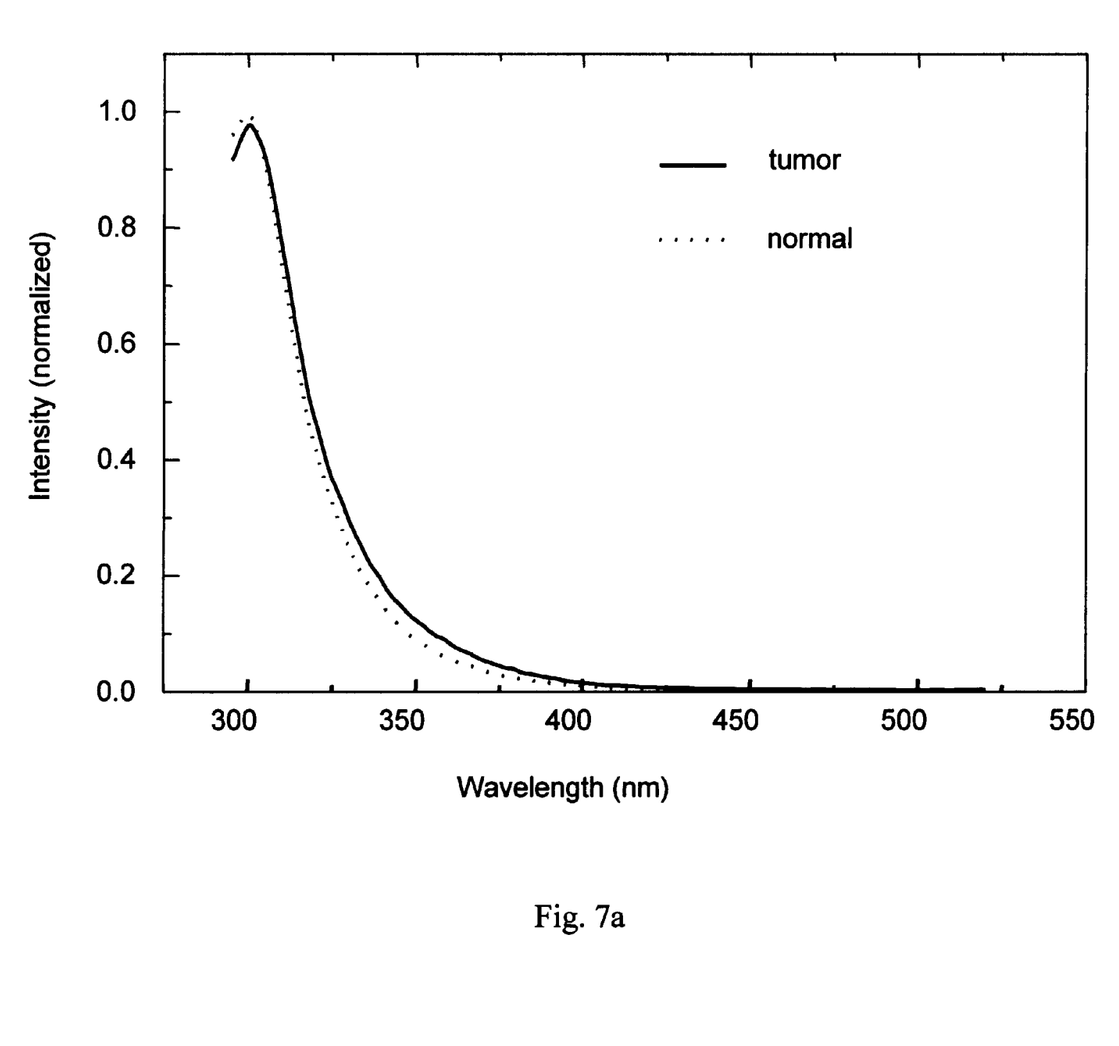
FIGS. 7(a) through 7(c) are graphic representations of the averaged fluorescence emission spectra for normal cells and malignant cells excited at 275 nm, 285 nm and 310 nm, respectively.
Figure 7B:
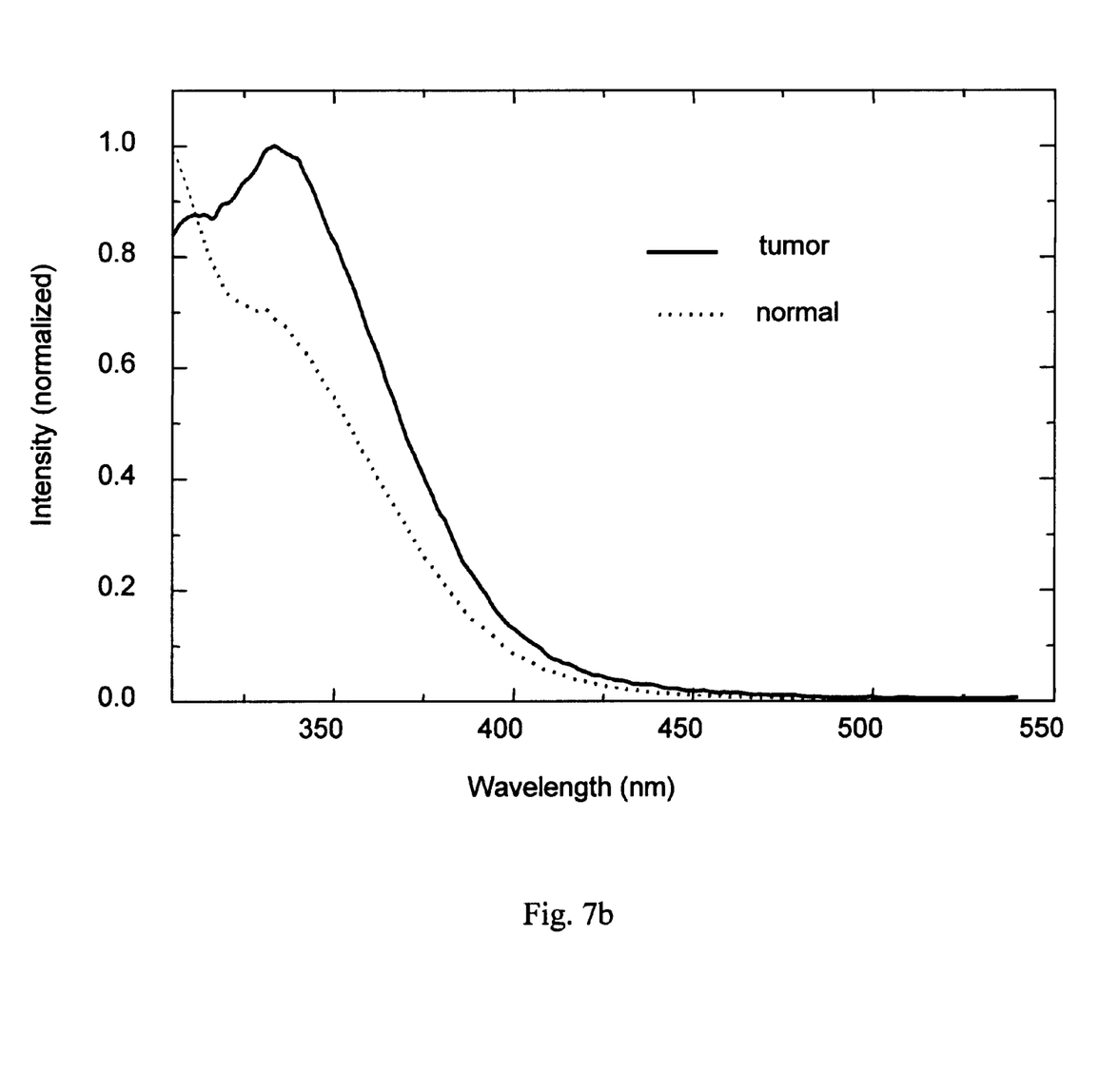
Figure 7C:
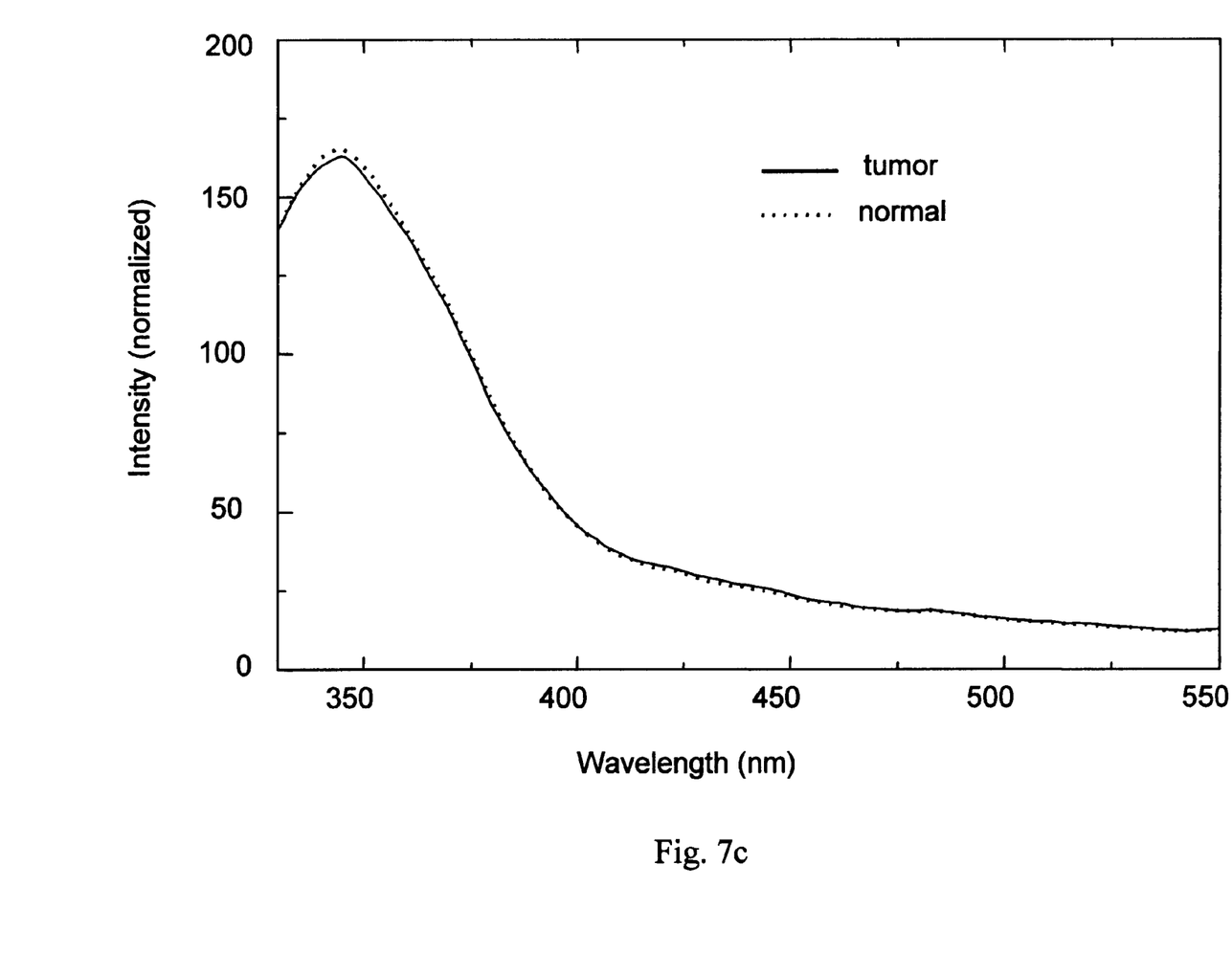

Fluorescence emission scans were measured for excitation wavelengths every 5 mm in the range of 250 to 310 nm. Three selected emission scans from normal and malignant cells for excitations at 275 nm (295–520 nm emission), 285 nm (305–540 nm emission) and 310 nm (330–560 nm emission) are shown in FIGS. 7(a) through 7(c), respectively. As can be seen in FIGS. 7(a) through 7(c), the wavelength of maximum emission differed depending on the excitation wavelength. (This phenomenon is not experienced when dealing with tissues as the emission spectra of tissues have the same maximum peak emission around 340 nm attributed to Trp irrespective of the excitation wavelengths in the region between 250 and 310 nm.) More particularly, the emission spectra at 275 nm excitation had a peak around 299 nm for both normal and malignant cells. The emission spectra for 285 nm excitation had two peaks around 310 nm and 335 nm for malignant cells and two peaks around 305 and 330 nm for normal cells. The averaged spectra for malignant cells experienced a small red shift as compared to the normal cells. This may be due to the presence of both Tyr and Trp at this excitation. For excitation at 310 nm, the averaged emission spectra for both the normal and malignant cells have similar spectral characteristics and no difference was observed at both 340 nm and 440 nm emission. The lack of a difference at 340 and 440 nm emission for 310 nm excitation result is most likely due to the absence of collagen and elastin in cells.

The excitation spectra of normal and malignant cells have similar spectral characteristics to those of benign and malignant tissues. The differences in the excitation spectra for 340 nm emission between benign and malignant tissues are due to key amino acid residues, e.g., tryptophan, tyrosine, phenylalanine, in cellular proteins. Differences between cells and tissues are due, in part, to the absence in cells of structural proteins like collagen and elastin. The change in the spectrum of cells may be due to the change in the optical absorption by the aforementioned amino acids and consequently to the proteins. The decreased absorption below 289 nm and the increased absorption above 289 nm for malignant cells and a red shift in the spectral profile for malignant cells indicates that certain conformational and/or microenvironmental changes concerning the proteins have occurred. The similar difference in excitation between normal and malignant tissues and cells suggests changes in key proteins, such as BRCA and P53. The similarity of fluorescence emission in normal and malignant cells points to the absence of collagen and elastin in tissues, giving rise to observed spectral differences.

Figure 8:
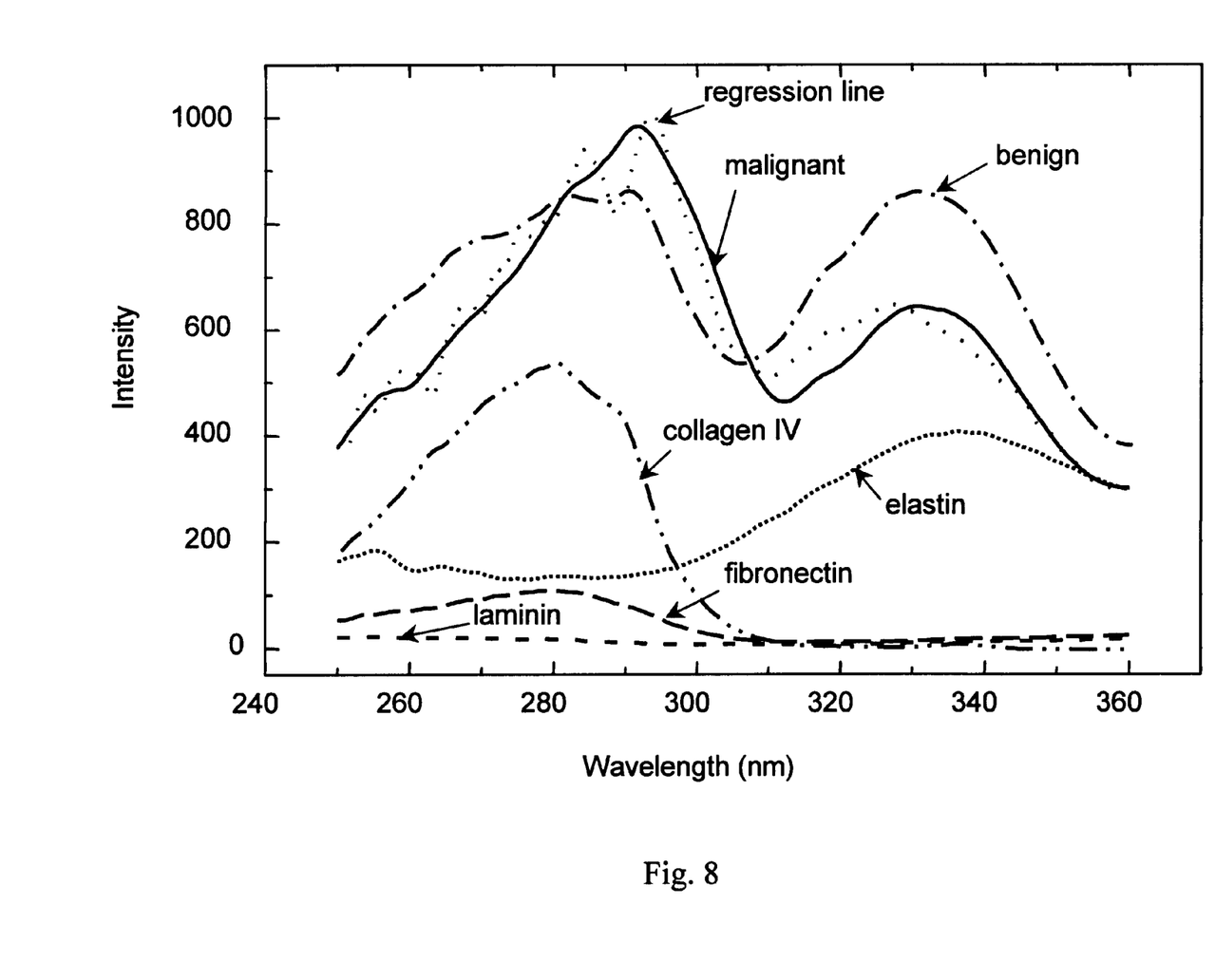
FIG. 8 is a graphic representation of the excitation spectra measured at 380 nm emission of various tissue matrix proteins, as well as of malignant and benign tissues.
Figure 9:
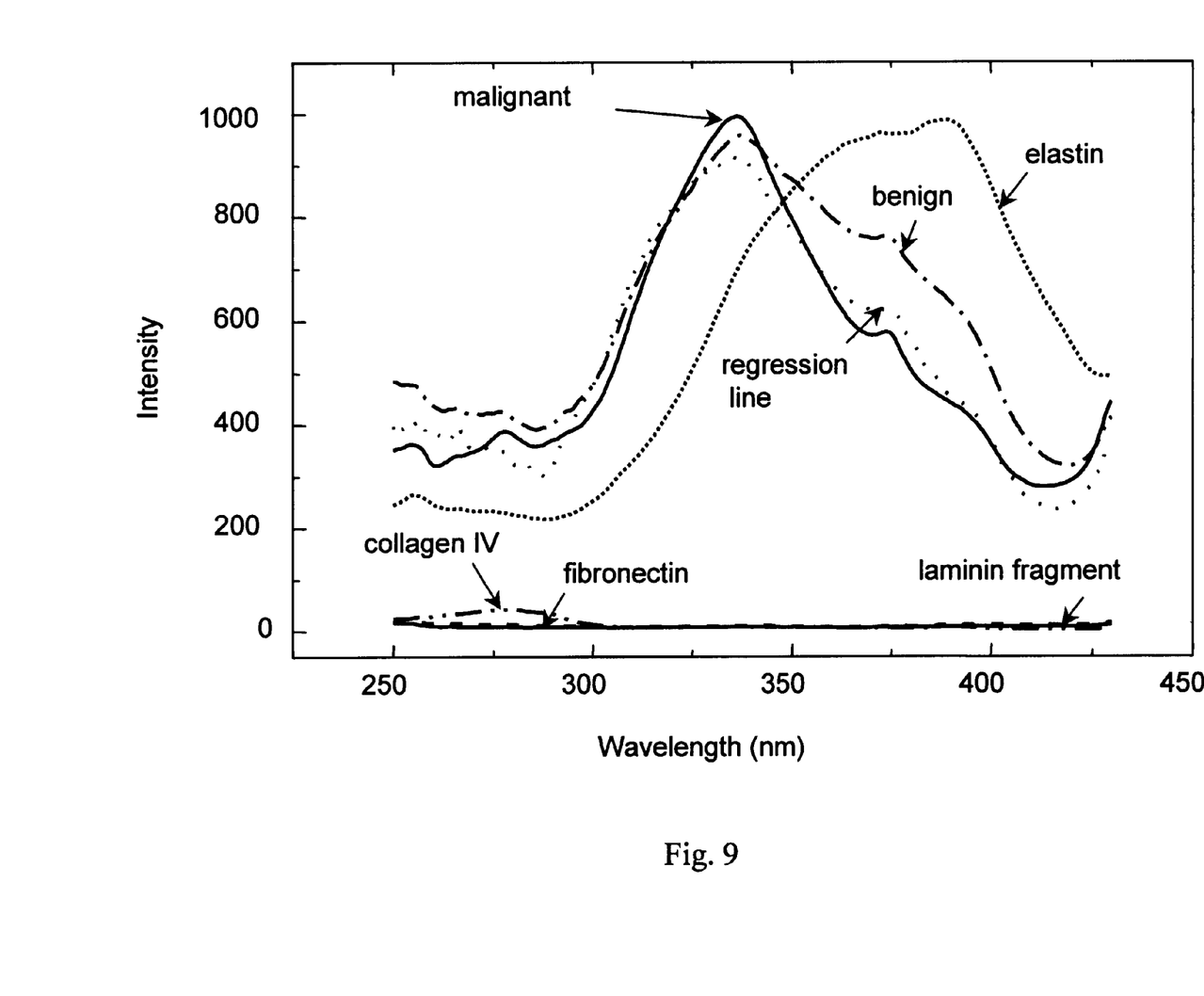
FIG. 9 is a graphic representation of the excitation spectra measured at 450 nm emission of various tissue matrix proteins, as well as of malignant and benign tissues.

Although not wishing to be limited to any particular theory behind the invention, the present inventors believe that the differences in the excitation spectra of benign and malignant breast tissues are related to tissue matrix proteins and special protein found in the malignant cytoplasm. The differences in the excitation spectrum of malignant tissue at 340 nm emission can be connected to a decrease therein of protein collagen IV and laminin fragment and to an increase therein of fibronectin protein. These results are consistent with results which are observed by biochemistry. Other two excitation spectra, measured at 380 nm and 450 nm emission (see FIGS. 8 and 9, respectively), connected to matrix proteins get the similar results that protein collagen IV, laminin fragment and elastin is decreased and fibronectin is increased.

The averaged excitation spectrum of normal breast tissue curve can be fitted by averaged malignant breast tissue plus tyrosine plus tryptophan or averaged malignant breast tissue curve can be fitted by averaged normal breast tissue curve minus tyrosine and minus tryptophan. The difference between normal and malignant can also be related to the quantities of amino acids being different.

There are key proteins which can account for the changes observed in excitation spectra of FIG. 1. These are collagen IV, laminin fragment, elastin and fibronectin.

Although not wishing to be limited to any particular theory behind the invention, the present inventors believe that proteins in the matrix cause the change in the region below 290 nm and proteins and amino acids are responsible for the region above 290 nm.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method of detecting cancer or a precancerous condition in a tissue, said method comprising the steps of:
   (a) illuminating the tissue with substantially monochromatic light of a first excitation wavelength so as to cause the tissue to emit native fluorescence at an emission wavelength, said first excitation wavelength being in the range of about 250 nm to about 320 nm, said emission wavelength being in the range of about 330 nm to about 400 nm;
   (b) measuring the intensity of native fluorescence at said emission wavelength caused by excitation of said tissue at said first excitation wavelength;
   (c) illuminating the tissue with substantially monochromatic light of a second excitation wavelength so as to cause the tissue to emit native fluorescence at said emission wavelength, said second excitation wavelength being in the range of about 250 nm to about 320 nm;
   (d) measuring the intensity of native fluorescence at said emission wavelength caused by excitation of said tissue at said second excitation wavelength;
   (e) calculating a ratio of intensities measured at said emission wavelength corresponding to excitation at said first and second excitation wavelengths; and
   (f) determining whether or not the tissue is cancerous or precancerous based on said ratio.

2. The method as claimed in claim 1 wherein said emission wavelength and said first and second excitation wavelengths are selected so that the native fluorescence emitted from the tissue at said emission wavelength after excitation at said first excitation wavelength is indistinguishable between normal tissues, on one hand, and cancerous or precancerous tissues, on the other hand, and so that the native fluorescence emitted from the tissue at said emission wavelength after excitation at said second excitation wavelength is distinguishable between normal tissues, on one hand, and cancerous or precancerous tissues, on the other hand.

3. The method as claimed in claim 2 wherein said emission wavelength is about 340 nm.

4. The method as claimed in claim 3 wherein said first excitation wavelength is about 289 nm.

5. The method as claimed in claim 4 wherein said second excitation wavelength is about 268 nm.

6. The method as claimed in claim 5 wherein said determining step comprises determining whether said ratio of $I_{289}/I_{268}$ is greater than 1.5 whereby the tissue is cancerous or precancerous or less than 1.5 whereby the tissue is not cancerous or precancerous.

7. The method as claimed in claim 4 wherein said second excitation wavelength is about 300 nm.

8. The method as claimed in claim 7 wherein said determining step comprises determining whether said ratio of $I_{289}/I_{300}$ is less than 1.5 whereby the tissue is cancerous or precancerous or greater than 1.5 whereby the tissue is not cancerous or precancerous.

9. The method as claimed in claim 1 wherein said determining step comprises comparing said ratio to ratios obtained from tissues whose condition is known.

10. The method as claimed in claim 1 wherein the tissue is a tissue selected from a part of the body consisting of the breast, cervix, colon, GI tract, ADT tract, GYN tract, brain, lung, kidney, bladder, prostate, skin, ovary, liver and stomach.

11. The method as claimed in claim 10 wherein said illuminating and measuring steps are performed in vivo inside a patient's body.

12. The method as claimed in claim 11 further comprising the step of removing said tissue from a patient's body if said tissue tests positive for cancer or a precancerous condition.

13. The method as claimed in claim 10 wherein said illuminating and measuring steps are performed in vitro.

14. The method as claimed in claim 1 further comprising monitoring and screening a patient for a particular cancer when the tissue tested tests positive for possible future development of a cancer.

15. A method of detecting cancer or a precancerous condition in a tissue, said method comprising the steps of:
   (a) illuminating the tissue with substantially monochromatic light of a first excitation wavelength so as to cause the tissue to emit native fluorescence at an emission wavelength, said first excitation wavelength being in the range of about 260 nm to about 340 nm, said emission wavelength being in the range of about 350 nm to about 450 nm;
   (b) measuring the intensity of native fluorescence at said emission wavelength caused by excitation of said tissue at said first excitation wavelength;
   (c) illuminating the tissue with substantially monochromatic light of a second excitation wavelength so as to cause the tissue to emit native fluorescence at said emission wavelength, said second excitation wavelength being in the range of about 260 nm to about 340 nm;
   (d) measuring the intensity of native fluorescence at said emission wavelength caused by excitation of said tissue at said second excitation wavelength;
   (e) calculating a ratio of intensities measured at said emission wavelength corresponding to excitation at said first and second excitation wavelengths; and
   (f) determining whether or not the tissue is cancerous or precancerous based on said ratio.

16. The method as claimed in claim 15 wherein said emission wavelength and said first and second excitation wavelengths are selected so that the native fluorescence emitted from the tissue at said emission wavelength after excitation at said first excitation wavelength is indistinguishable between normal tissues, on one hand, and cancerous or precancerous tissues, on the other hand, and so that the native fluorescence emitted from the tissue at said emission wavelength after excitation at said second excitation wavelength is distinguishable between normal tissues, on one hand, and cancerous or precancerous tissues, on the other hand.

17. The method as claimed in claim 15 wherein the tissue is a tissue selected from a part of the body consisting of the breast, cervix, colon, GI tract, ADT tract, GYN tract, brain, lung, kidney, bladder, prostate, skin, ovary, liver and stomach.

18. A method of detecting cancer or a precancerous condition in a cell, said method comprising the steps of:
   (a) illuminating the cell with substantially monochromatic light of a first excitation wavelength so as to cause the cell to emit native fluorescence at an emission wavelength, said first excitation wavelength being in the range of about 250 nm to about 320 nm, said emission wavelength being in the range of about 330 nm to about 400 nm;

(b) measuring the intensity of native fluorescence at said emission wavelength caused by excitation of said cell at said first excitation wavelength;

(c) illuminating the cell with substantially monochromatic light of a second excitation wavelength so as to cause the cell to emit native fluorescence at said emission wavelength, said second excitation wavelength being in the range of about 250 nm to about 320 nm;

(d) measuring the intensity of native fluorescence at said emission wavelength caused by excitation of said cell at said second excitation wavelength;

(e) calculating a ratio of intensities measured at said emission wavelength corresponding to excitation at said first and second excitation wavelengths; and (f) determining whether or not the cell is cancerous or precancerous based on said ratio.

19. The method as claimed in claim 18 wherein said emission wavelength and said first and second excitation wavelengths are selected so that the native fluorescence emitted from the cell at said emission wavelength after excitation at said first excitation wavelength is indistinguishable between normal cells, on one hand, and cancerous or precancerous cells, on the other hand, and so that the native fluorescence emitted from the cell at said emission wavelength after excitation at said second excitation wavelength is distinguishable between normal cells, on one hand, and cancerous or precancerous cells, on the other hand.

20. The method as claimed in claim 19 wherein said emission wavelength is about 340 nm.

21. The method as claimed in claim 20 wherein said first excitation wavelength is about 289 nm.

22. The method as claimed in claim 21 wherein said second excitation wavelength is about 250 nm.

23. The method as claimed in claim 22 wherein said determining step comprises determining whether said ratio of $I_{289}/I_{250}$ is greater than 1.7 whereby the cell is cancerous or precancerous or less than 1.7 whereby the cell is not cancerous or precancerous.

24. The method as claimed in claim 21 wherein said second excitation wavelength is about 297 nm.

25. The method as claimed in claim 24 wherein said determining step comprises determining whether said ratio of $I_{289}/I_{297}$ is less than 1.5 whereby the cell is cancerous or precancerous or greater than 1.5 whereby the cell is not cancerous or precancerous.

26. The method as claimed in claim 18 wherein said determining step comprises comparing said ratio to ratios obtained from cells whose condition is known.

27. The method as claimed in claim 18 wherein the cell is a cell selected from a part of the body consisting of the breast, cervix, colon, GI tract, ADT tract, GYN tract, brain, lung, kidney, bladder, prostate, skin, ovary, liver and stomach.

28. The method as claimed in claim 18 wherein said illuminating and measuring steps are performed in vitro.

29. The method as claimed in claim 18 wherein the cell is a cultured cell.

30. The method as claimed in claim 18 wherein the cell is present in a body fluid.

31. A method of detecting cancer or a precancerous condition in a cell, said method comprising the steps of:

(a) illuminating the cell with substantially monochromatic light of a first excitation wavelength so as to cause the cell to emit native fluorescence at an emission wavelength, said first excitation wavelength being in the range of about 260 nm to about 340 nm, said emission wavelength being in the range of about 350 nm to about 450 nm;

(b) measuring the intensity of native fluorescence at said emission wavelength caused by excitation of said cell at said first excitation wavelength;

(c) illuminating the cell with substantially monochromatic light of a second excitation wavelength so as to cause the cell to emit native fluorescence at said emission wavelength, said second excitation wavelength being in the range of about 260 nm to about 340 nm;

(d) measuring the intensity of native fluorescence at said emission wavelength caused by excitation of said cell at said second excitation wavelength;

(e) calculating a ratio of intensities measured at said emission wavelength corresponding to excitation at said first and second excitation wavelengths; and (f) determining whether or not the cell is cancerous or precancerous based on said ratio.

32. The method as claimed in claim 31 wherein said emission wavelength and said first and second excitation wavelengths are selected so that the native fluorescence emitted from the cell at said emission wavelength after excitation at said first excitation wavelength is indistinguishable between normal cells, on one hand, and cancerous or precancerous cells, on the other hand, and so that the native fluorescence emitted from the cell at said emission wavelength after excitation at said second excitation wavelength is distinguishable between normal cells, on one hand, and cancerous or precancerous cells, on the other hand.

33. The method as claimed in claim 31 wherein the cell is a cell selected from a part of the body consisting of the breast, cervix, colon, GI tract, ADT tract, GYN tract, brain, lung, kidney, bladder, prostate, skin, ovary, liver and stomach.

34. The method as claimed in claim 31 wherein said illuminating and measuring steps are performed in vitro.

35. The method as claimed in claim 31 wherein the cell is a cultured cell.

36. The method as claimed in claim 31 wherein the cell is present in a body fluid.

37. A method of detecting the presence of a cancer-related protein in a sample, said method comprising the steps of:

(a) illuminating the sample with substantially monochromatic light of a first excitation wavelength so as to cause the sample to emit native fluorescence at an emission wavelength, said first excitation wavelength being in the range of about 250 nm to about 320 nm, said emission wavelength being in the range of about 330 nm to about 400 nm;

(b) measuring the intensity of native fluorescence at said emission wavelength caused by excitation of said sample at said first excitation wavelength;

(c) illuminating the sample with substantially monochromatic light of a second excitation wavelength so as to cause the sample to emit native fluorescence at said emission wavelength, said second excitation wavelength being in the range of about 250 nm to about 320 nm;

(d) measuring the intensity of native fluorescence at said emission wavelength caused by excitation of said sample at said second excitation wavelength;

(e) calculating a ratio of intensities measured at said emission wavelength corresponding to excitation at said first and second excitation wavelengths; and (f) determining whether or not the sample contains the cancer-related protein based on said ratio.

38. The method as claimed in claim 37 wherein said cancer-related protein is BRCA-1 protein.

39. The method as claimed in claim 37 wherein said sample is one of a tissue sample and a cell sample.

40. The method as claimed in claim 39 wherein said sample is a tissue sample and wherein said emission wavelength is about 340 nm, said first excitation wavelength is about 289 nm and said second excitation wavelength is about 268 nm.

41. The method as claimed in claim 39 wherein said sample is a tissue sample and wherein said emission wavelength is about 340 nm, said first excitation wavelength is about 289 nm and said second excitation wavelength is about 300 nm.

42. The method as claimed in claim 39 wherein said sample is a cell sample and wherein said emission wavelength is about 340 nm, said first excitation wavelength is about 289 nm and said second excitation wavelength is about 250 nm.

43. The method as claimed in claim 39 wherein said sample is a cell sample and wherein said emission wavelength is about 340 nm, said first excitation wavelength is about 289 nm and said second excitation wavelength is about 297 nm.

* * * * *